United States Patent [19]
Kosaka

[11] Patent Number: 5,050,987
[45] Date of Patent: Sep. 24, 1991

[54] PARTICLE ANALYZING APPARATUS AND METHOD FOR DETERMINING NUCLEAR SHIFT INDEX

[75] Inventor: Tokihiro Kosaka, Hyogo, Japan

[73] Assignee: Toa Medical Electronics Co., Ltd., Kobe, Japan

[21] Appl. No.: 402,866

[22] Filed: Sep. 1, 1989

[51] Int. Cl.[5] ..................... G01N 33/48; G01N 21/69; G01N 21/64

[52] U.S. Cl. ........................................ 356/73; 356/39; 250/461.2

[58] Field of Search ....................... 356/39, 72, 73, 40, 356/337, 338, 343; 364/408, 413.1, 413.08; 250/568, 214 DC, 461.1, 461.2

[56] References Cited

U.S. PATENT DOCUMENTS 4,790,653 12/1988 North, Jr. ............................ 356/73

OTHER PUBLICATIONS

Journal of Histochemistry & Cytochemistry; vol. 27, pp. 321–324, 1979.

*Primary Examiner*—Vincent P. McGraw
*Assistant Examiner*—La Charles P. Keesee
*Attorney, Agent, or Firm*—Fitch, Even, Tabin & Flannery

[57] ABSTRACT

A particle suspension is irradiated with a laser beam, and scattered light from a single particle irradiated in an irradiating zone is detected as a plurality of particle signals. The laser beam in the irradiating zone is formed to be narrower than the diameter of a particle nucleus in the direction of particle flow and wider than the diameter of the particle in a direction perpendicular to the particle flow. The degree of complexity of the particle nucleus is determined from high-frequency signal components contained in one type of particle signal based on side-scattered light from one particle, and the degree of symmetry of the particle nucleus is determined from the magnitude of a difference between two types of particle signals based on side-scattered light from one particle. The degrees of complexity and symmetry of the particle nucleus serve as data for particle analysis.

12 Claims, 8 Drawing Sheets

50 FIRST CHARACTERISTIC QUANTITY EXTRACTING MEANS
62
DIFFERENTIATOR
64
RECTIFIER
66
INTEGRATOR
68
A/D CONVERTER
FIRST PARTICLE SIGNAL
SECOND PARTICLE SIGNAL
+
SUBTRACTOR
−
70
RECTIFIER
72
INTEGRATOR
74
A/D CONVERTER
76
52 SECOND CHARACTERISTIC QUANTITY EXTRACTING MEANS

54 FIRST CHARACTERISTIC QUANTITY EXTRACTING MEANS
56 SECOND CHARACTERISTIC QUANTITY EXTRACTING MEANS
FIRST PARTICLE SIGNAL
SECOND PARTICLE SIGNAL
80 A/D CONVERTER
78 CLOCK GENERATOR
88 A/D CONVERTER
82 BUFFER
84 SUBTRACTOR
90 SUBTRACTOR
86 ACCUMULATOR
92 ACCUMULATOR
+
-

FIRST PARTICLE SIGNAL
DELAY ELEMENT
96
LOW-PASS FILTER
94
SUBTRACTOR
98
+
−
RECTIFIER
100
INTEGRATOR
102
104

FIRST PARTICLE SIGNAL
A/D CONVERTER
108
CLOCK GENERATOR
106
BUFFER
110
DIGITAL FILTER
112
SUBTRACTOR
114
+
−
116
+
+

CELL TYPE
IMMATURE NEUTROPHILS
MATURE NEUTROPHILS
SEGMENTED NEUTROPHILS
MYELOBLAST
PROMYELOCYTE
MYELOCYTE
METAMYELOCYTE
BAND NEUTROPHIL
2 LOBES
3 LOBES
4 LOBES
5 OR MORE LOBES
NEUTROPHIL DISTRIBUTION CURVE
%
60
50
40
30
20
10
[LEFT-SHIFT (EXTREME)]
(LEUKEMIA)
[LEFT-SHIFT]
(INFECTION)
[NORMAL]
[RIGHT-SHIFT]
(PERNICIOUS ANEMIA)

PARTICLE ANALYZING APPARATUS AND METHOD FOR DETERMINING NUCLEAR SHIFT INDEX

BACKGROUND OF THE INVENTION

1. Field of the Invention

This invention relates to a particle analyzing apparatus and method for measuring the nuclear shift index of particles by suitably preparing a liquid specimen such as blood, passing particles such as white blood cells contained in the specimen through a detecting zone to detect signals corresponding to the particles, and processing the detected signals.

2. Description of the Prior Art

White blood cells present in human blood are classified into monocytes, neutrophils, eosinophiles and basophils, and determining the numbers of particles according to class or the content of these particles as a percentage is a useful tool in clinical examination. Accordingly, in order to classify white blood cells into the aforementioned particles and enumerate the same automatically, apparatus heretofore developed for this purpose are adapted to dilute blood with a diluent, supply the diluted blood to a detector to detect any electrical or optical change produced when the blood cells pass through the detector, classify the particles and count the same.

A first conventional apparatus of this kind is adapted to destroy red blood cells by using a hemolytic agent to obtain an electrolyte in which only white blood cells are suspended, pass the electrolyte through a detector provided with pores, and detect a change in electrical impedance (e.g., electrical resistance) at the porous portion, the change occurring when white blood cells pass through the pores. This apparatus enables white blood cells to be identified based on a difference in the magnitude of the detected signal.

A second conventional apparatus is adapted to pass a dilute solution of blood, which is in the form of a fine stream, through the central portion of a flow cell, and irradiate the fine stream with light to detect an optical change, such as a change in fluorescence or scattered light, produced when the blood flows through the cell. With this apparatus, white blood cells can be identified based on a difference in fluorescent intensity or intensity of scattered light detected by staining the white blood cells.

The porous portion constituting the detecting section of the first conventional apparatus covers an area that is considerably large in comparison with particle size. For this reason, particles cannot be detected on a microscopic scale. By way of example, if particles having a diameter of several microns are to be detected, the pores would have to possess a hole diameter and pass length on the order of tens of microns to 100 microns in order to prevent clogging. In addition, the only information acquired relates to particle size.

With the second conventional apparatus, the detecting zone can be made smaller than the size of the particles by narrowing down the irradiating light flux. By this reducing the size of the detecting zone, particles can be detected on a microscopic scale. In other words, various intrinsic characteristics possessed by the particles can be detected in greater detail, so that a greater amount of information can be extracted.

For example, as set forth in the "Bulletin of the Electrotechnical Laboratory" by Yoshio Nomura, Vol. 44, No. 3, pp. 185–186, and in "Flow Cytometry and Sorting" by L. L. Wheeless, et al., pp. 125–135, an apparatus is available in which irradiation is performed using a slit-shaped laser beam. Specifically, as shown in FIG. 10, a slit-shaped laser beam 124 having a width of approximately 4 μm is projected in a direction perpendicular to that of cell flow, and fluorescent profile is measured when the cells cross the laser beam 124. The detection signal thus obtained is illustrated in FIG. 11. Signal widths C and N are commensurate with the diameters of cell 120 and nucleus 122. Accordingly, the ratio of nuclear diameter to cell diameter is obtained from N/C. Using the slit beam also makes it possible to take measurements to determine whether polynuclear cells are present.

Further, in "Cytometry" by L. L. Wheeless, et al., Vol. 5, pp. 1–8, an example is described in which detection error ascribable to cell orientation is prevented. To this end, an X-Y-Z slit scanning method is used in which X and Y axes are taken in a plane containing the slit beam and the direction of cell flow is taken as the Z axis, with the fluorescent profile being analyzed in the X, Y and Z directions. Both parameters, namely the N/C ratio and nuclear fluorescent intensity obtained, are used to enable cell discrimination.

A problem encountered with the first conventional apparatus is that only particle size information can be obtained, as mentioned earlier. Therefore, in order to classify and quantify white blood cells, it is required that the group of white blood cells in each class be made large enough to enable it to be distinguished from groups of white blood cells in other classes. This means that the hemolytic agent must be carefully selected, and that measurements must be taken while strictly controlling such measurement conditions as temperature. However, since the detection principle from the outset is based on particle size, this would make it impossible to detect the various characteristics possessed by the particles. For example, it would not be possible to detect the state of nuclear shift of the cells.

An advantage of the second conventional apparatus is that many characteristics can be detected from a single particle by reducing the size of the detecting zone, as mentioned above. However, nowhere does the aforementioned literature describe determining the nuclear shift index of white blood cells, which is one characteristic possessed by white blood cells, or a technique for achieving this.

Nuclear shift index rises as the maturity of white blood cell granulocytes progresses. FIG. 12 is a view for describing the nuclear shift of neutrophils cited in "Clinical Laboratory Methods" by Masamitsu Kanai, et al., 28th Edition, Vol. 6, p. 50. An increase in neutrophils with a small number of lobes is referred to as "left shift". If an increase in the total number of white blood cells appears at this time, this indicates a highly active myeloid function and the likelihood of leukemia. If a reduction in the total number of white blood cells appears, myeloid function is considered to be impaired and the patient is readily susceptible to infection. An increase in neutrophils with large number of lobes is referred to as "right shift". There is often a decrease in the total number of white blood cells in this case as well. This is considered to indicate pernicious anemia.

Thus, determining the lobe state of specific cellular nuclei in various white blood cells by examination has great clinical significance.

SUMMARY OF THE INVENTION

The present invention is intended to meet this demand and its object is to provide an apparatus and method through which an index (shift index) indicating the lobe state of cellular nuclei can be obtained for every white blood cell by irradiating particles with a finely converged laser beam and processing signals indicative of particles detected in directions symmetrical with respect to the optic axis of the laser beam.

The particle analyzing apparatus and method of the invention are based on the following principle: when a particle stream is irradiated with a laser beam narrow in the direction of particle flow and wide in the direction perpendicular to the particle flow, the waveform of the detection signal becomes more complicated the more complex the shape of the particle nucleus. By extracting such characteristics as the degree of complexity of the detection signal waveform, the nuclear shift index of the particle is measured to enable analysis of particles such as white blood cells.

The present invention provides a particle analyzing apparatus for passing a liquid suspension in the form of a sheathed stream, forming a detecting zone by irradiating a zone, in which particles flow substantially in single file in the direction of flow, with a laser beam in a direction perpendicular to the direction of particle flow, and detecting, at a plurality of locations, an optical change in scattered light or fluorescent light which is produced by particles passing through the detecting zone one at a time, thereby obtaining plural types of signals with respect to a single particle, the apparatus characterized by comprising means for projecting the laser beam so as to be narrower than the diameter of a particle nucleus in the direction of particle flow and wider than the diameter of the particle in a direction perpendicular to the particle flow, means for detecting two types of particle signals with respect to a single particle by detecting side-scattered light produced in directions symmetrical with respect to the optic axis of the laser beam, first characteristic quantity extracting means for extracting the amount of high-frequency components, which are contained in at least one type of particle signal of the two types of particle signals, in order to determine the complexity of the particle nucleus, and second characteristic quantity extracting means for extracting the amount of a difference between the two types of particle signals in order to determine the symmetry of the particle nucleus.

The particle analyzing method of the invention is characterized by obtaining a nuclear shift index for every symmetry of a single particle using particle nucleus complexity data obtained by the first characteristic quantity extracting means and particle nucleus data obtained by the second characteristic quantity extracting means.

The first characteristic quantity extracting means for extracting particle nucleus complexity can comprise a differentiator for differentiating an inputted particle signal, a rectifier connected to an output side of the differentiator for full-wave rectifying the output signal thereof, an integrator connected to an output side of the rectifier for integrating an output signal thereof, and an A/D converter connected to an output side of the integrator for converting an analog output thereof into digital data.

Further, in order to implement the function of the first characteristic quantity extracting means by digital signal processing, the first characteristic quantity extracting means can comprise an A/D converter for sampling and successively converting the inputted particle signal into digital data at equally spaced clock pulses, memory means connected to an output side of the A/D converter for temporarily storing the digital data, a subtracter connected to the output side of the A/D converter and an output side of the memory means for successively calculating the absolute value of a difference between data, which prevails at the present time, outputted by the A/D converter and data, which prevailed one clock interval earlier than the present time, outputted by the memory means, and an accumulator connected to an output side of the subtracter for successively cumulatively adding data outputted by the subtracter.

The second characteristic quantity extracting means for extracting the symmetry of the particle nucleus can comprise a subtracter for obtaining the difference between the inputted two types of particle signals, a rectifier connected to an output side of the subtracter for full-wave rectifying an output signal thereof, an integrator connected to an output side of the rectifier for integrating an output signal thereof, and an A/D converter connected to an output side of the integrator for converting an analog output thereof into digital data.

Further, in order to implement the function of the second characteristic quantity extracting means by digital signal processing, the second characteristic quantity extracting means can comprise an A/D converter for sampling and successively converting each of the inputted two types of particle signals into digital data at equally spaced clock pulses, a subtracter connected to an output side of the A/D converter for successively calculating the absolute value of a difference between both items of digital data, and an accumulator connected to an output side of the subtracter for successively cumulatively adding data outputted by the subtracter.

In operation, the suspension of blood particles is passed in the form of a sheathed stream and is irradiated with a laser beam the width whereof is smaller than the diameter of the particle nucleus in the direction of particle flow and larger than the diameter of the particle in the direction perpendicular to the particle flow. By passing the particle through the detecting zone, which is the zone irradiated, scattered light conforming to the structure of the particle nucleus is generated. Accordingly, by detecting this optical change, a particle signal which includes information relating to the structure of the nucleus can be obtained. More specifically, there is a relationship between complexity of cell shape and the complexity of the particle signal waveform. By extracting the amount of components in the high-frequency region contained in the particle signal waveform by the first characteristic quantity extracting means, the complexity of the waveform can be extracted and it is possible to determine the complexity of the particle nucleus in a case where the particle is viewed from a certain side face thereof.

If the optical change is detected at a plurality of locations, one particle can be observed from a number of its side faces. In particular, if the side-scattered light beams produced in directions symmetrical with respect to the optic axis of the laser by a particle in the irradiating zone are each detected and the two types of particle signals obtained are compared, the degree of symmetry of the nuclear shape can be ascertained. Accordingly, the magnitude of the difference between the two types of particle signals is extracted by the second characteristic quantity extracting means to obtain the symmetry of the particle nucleus. Further, if the data indicative of the complexity and symmetry of the nucleus obtained by the first and second characteristic quantity extracting means are used, the nuclear shift index can be calculated without relation to the orientation of the particle when it passed through the detecting zone.

The foregoing operation will now be explained in further detail in conformity with the embodiment of the invention described later.

The particle signal is differentiated by a differentiator 62, whereby the components in the high-frequency region are extracted. Next, the differentiated signal relating to these components in the high-frequency region is full-wave rectified by a rectifier 64, and the output whereof is integrated by an integrator 66 to obtain the area of the waveform of the differentiated signal. In other words, the amount of complexity of the particle signal waveform is delivered to the integrator 66, the analog output of which is converted into digital data by an A/D converter 68 in order to obtain a numerical value. Thus, the components in the high-frequency region contained in the particle signal are extracted.

The particle signal is sampled and successively converted into digital data at equally spaced clock pulses by an A/D converter 80. These data are temporarily retained in memory means 82 in successive fashion and then are outputted sequentially. A subtracter 84 successively calculates the absolute value of the difference between the digitized data, which prevails at the present time, outputted by the A/D converter 80, and the digitized data, which prevailed one clock interval earlier than the present time, outputted by the memory means 28. The absolute value of this difference is successively cumulatively added by an accumulator 86 to obtain a numerical value. Thus, the components in the high-frequency region contained in the particle signal are extracted.

The difference between the two types of particle signals is obtained by a subtracter 70. The different signal is then full-wave rectified by a rectifier 72, the output of which is integrated by an integrator 74 to obtain the area of the difference signal waveform. In other words, a signal indicating the magnitude of the difference between the particle signal waveforms is delivered to the integrator 74, the analog output of which is converted into digital data by an A/D converter 76 in order to obtain a numerical value. Thus, the magnitude of the difference between the two types of particle signals.

The two types of particle signals are respectively sampled by A/D converters 80, 88 and successively converted into digital data thereby. The absolute value of the difference between these two items of data is successively calculated by a subtracter 90. The absolute value is successively accumulatively added by an accumulator 92 to obtain a numerical value. The magnitude of the difference between the two types of particle signals is thus obtained The magnitude of the aforementioned difference is related to the particle nuclear shift index and serves as particle analysis data.

Other features and advantages of the present invention will be apparent from the following description taken in conjunction with the accompanying drawings.

BRIEF DESCRIPTION OF THE DRAWINGS

FIGS. 6 and 7 are diagrams for describing the first characteristic quantity extracting means, in which FIG. 6 shows particle signals and FIG. 7 signals obtained by differentiating the particle signals;

FIGS. 10 and 11 are diagrams illustrating the relationship between an irradiating laser beam and a signal, in which FIG. 10 shows the relationship between particles and a slit beam and FIG. 11 shows a particle signal obtained by detecting fluorescence;

DESCRIPTION OF THE PREFERRED EMBODIMENTS

Figure 1:
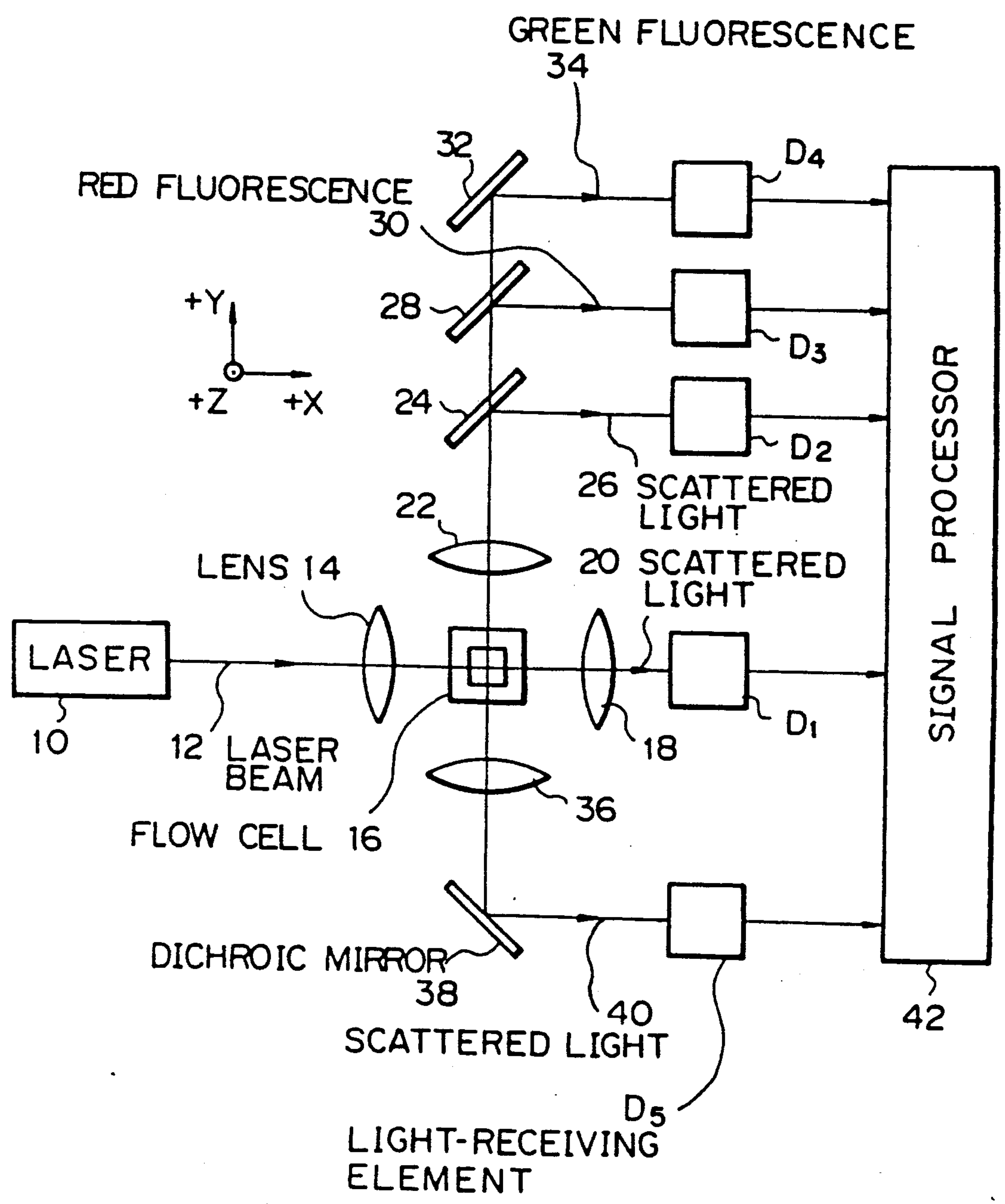
FIG. 1 is a schematic view illustrating an example of an optical system in the particle analyzing apparatus of the present invention.

FIG. 1 is a schematic view illustrating an example of an optical system for obtaining plural types of particle signals with respect to a single particle in a particle analyzing apparatus of the present invention. A laser beam 12 emitted by an argon laser 10 and propagating to the right in FIG. 1 (i.e., along the +X axis) irradiates a specimen of blood or the like which flows through a flow cell 16 in a direction perpendicular to the plane of the drawing (i.e., along the + or −Z axis). The laser beam 12 is condensed by a lens 14 to irradiate the central portion of the flow cell 16 with a beam width reduced along the +Y and −Y axes to the order of 100–150 μm, which is greater than particle diameter, and along the +Z and −Z axes to the order to 2–3 μm, which is less than the diameter of the particle nucleus.

Since it is desired here to measure the characteristics and number of white blood cells, the blood specimen passed through the flow cell 16 should satisfy the following conditions:

(a) Red blood cells, which far outnumber white blood cells, should be destroyed so as not to hamper measurement of the white blood cells.

(b) The treatment used to destroy the red blood cells should not cause a morphological change in the white blood cells (i.e., expansion, contraction, deformation, etc.)

Accordingly, the specimen should be treated by adding to it a first liquid exhibiting acidity (e.g., pH 4.5) and low osmotic pressure (e.g., an osmotic pressure of 50 mOsm/kg), incubating the specimen (for example, at 25° C. for 20 seconds), adding a second liquid exhibiting alkalinity (e.g., pH 9.8–9.9) and high osmotic pressure (e.g., an osmotic pressure of 2200 mOsm/kg), incubating the specimen (for example, at 25° C. for 40 seconds) and returning the specimen to the isotonic state (an isotonic pressure of 286 mOsm/kg). Since red blood cells exhibit little resistive pressure, they are destroyed by the acidic treatment at low osmotic pressure. White blood cells, on the other hand, possess a high resistive pressure and remain in the specimen without being destroyed. If desired, the first liquid may contain a fluorescent dye for staining the nuclei of the white blood cells.

With its periphery enveloped by a fluid sheath, the specimen passes through the central portion of the flow cell 16 in a fine stream. By passing the white blood cells through the detection zone, which is the zone irradiated by the laser beam, one at a time substantially in a single file in the direction of flow, scattered light or fluorescence is emitted in various directions conforming to the structure of each particle nucleus. If the structure of a nucleus is complex, then a complex optical signal will be emitted.

Forward-scattered light 20, namely scattered light emitted in the forward direction (along the +X axis), is partially shielded by a light-shielding plate (condensed by a lens 18) and detected by a photodiode $D_1$. Meanwhile, side-scattered light 26, 30, 34, namely light emitted to one side (along the +Y axis) is condensed by a lens 22. The scattered light 26 is reflected by a dichroic mirror 24, which has the ability to transmit and reflect selected wavelengths, and is detected by a photomultiplier tube $D_2$. Fluorescence 30, 34 passes throught the dichroic mirror 24. Red fluorescence 30 is reflected by a dichroic mirror 28 and detected by a photomultiplier tube $D_3$. Green fluorescence 34 is reflected by a dichroic mirror 32 and detected by a photomultiplier tube $D_4$.

Side-scattered light 40 is light emitted to the other side (along the −Y axis), which is a direction symmetrical to the above-mentioned first side direction with respect to the optic axis of the laser. This side-scattered light 40 is condensed by a lens 36, reflected by a dichroic mirror 38 and detected by a photomultiplier tube $D_5$.

Thus, plural types of signals are obtained with regard to a single-particle that passes through the detecting zone. The detected particle signals of the plurality of types are delivered to a signal processor 42 in order to be analyzed. In the present embodiment, the side-scattered light beam 26 along the +Y axis and the side-scattered light 40 along the −Y axis are detected by the light-receiving elements $D_2$, $D_5$, respectively, and the nuclear shift index of white blood cells is determined using the two types of particle signals obtained.

Ordinarily, a particle signal having a complex waveform is obtained if the shape of the particle nucleus is complex. Accordingly, the complexity of the shape of a nucleus can be found by applying the particle signal to first characteristic quantity extracting means and extracting the complexity of the signal waveform. However, merely detecting scattered light in one direction allows the complexity of the nucleus to be ascertained as seen only from one side face thereof, and using these data alone to determine the shift index of the nucleus would result in measurement error. Accordingly, in order to reduce the error, it is required that light scattered in a plurality of directions be detected. If there are many locations at which scattered light is detected, this will make it possible to determine the shape of the nucleus more correctly, with greater accuracy being achieved the greater the number of locations. Cost rises correspondingly, however. Therefore, as the result of much research, the inventor has found that if it is arranged to detect scattered light emitted in directions symmetrical with respect to the optic axis of the laser, measurement accuracy involved in particle analysis is greatly improved without requiring complicated equipment and operation and without greatly increased expenditures.

Particle signals obtained by detecting scattered light in symmetrical directions are considered to contain information indicative of nuclear shape when viewing the particle from positions symmetrical with respect to the optic axis.

The degree of nuclear symmetry can be ascertained by comparing the two particle signals using second characteristic quantity extracting means. It has been clarified that if the aforementioned data relating to the complexity of a nucleus and the data relating to the symmetry of the nucleus are employed, the shape of the nucleus can be suitably determined irrespective of the orientation of the particle as it passes through the detecting zone.

The degree of symmetry of a nucleus can be determined with especially good accuracy if the apparatus is arranged to detect the scattered light 26 lying at 90° (along the +Y axis) and the scattered light 40 lying at −90° (along the −Y axis) with respect to the optic axis of the laser, as shown in FIG. 1.

Figure 2:
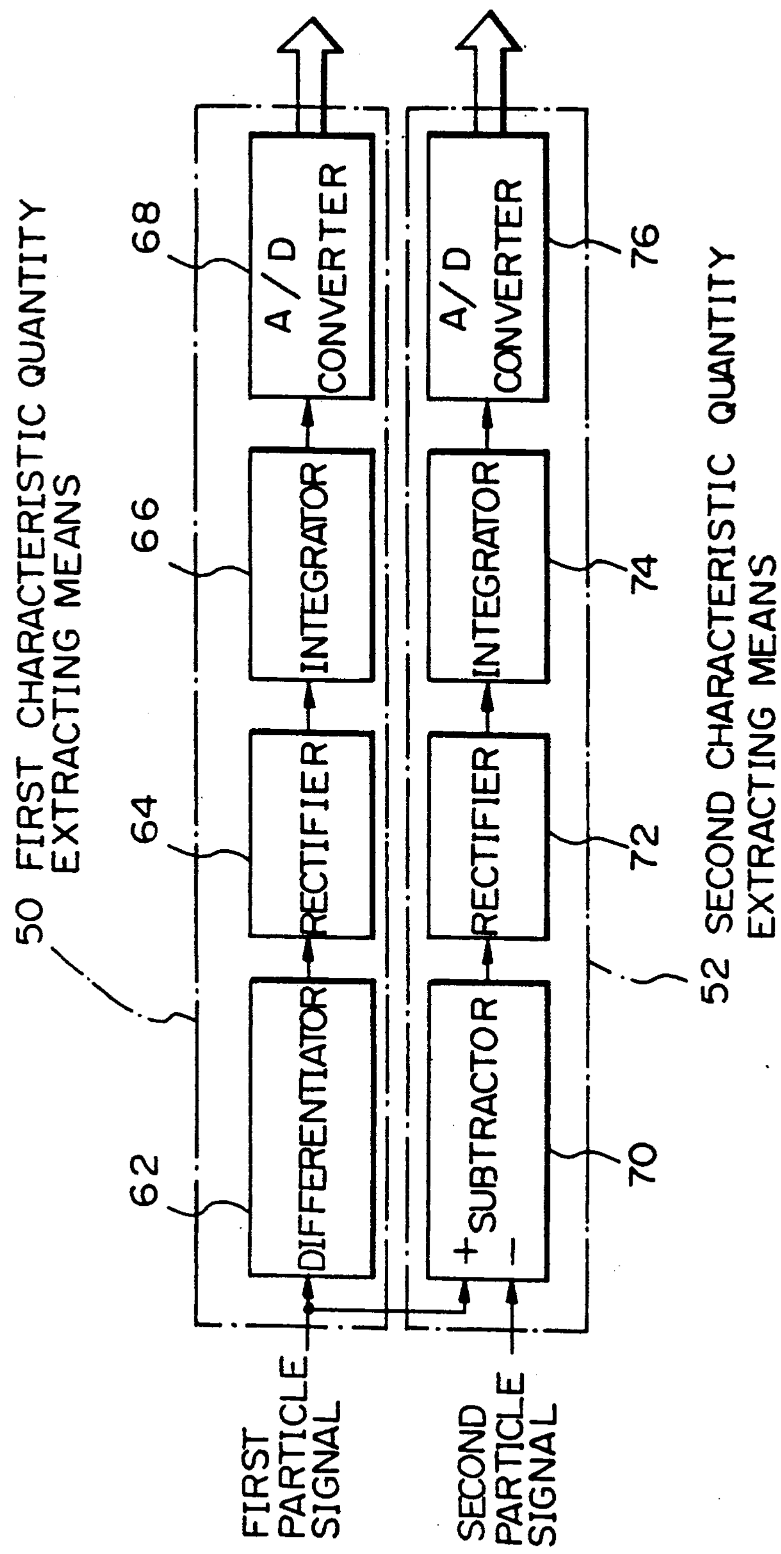
FIGS. 2 and 3 are block diagrams illustrating embodiments of characteristic quantity extracting means which jointly employs first characteristic quantity extracting means and second characteristic quantity extracting means.
Figure 6:
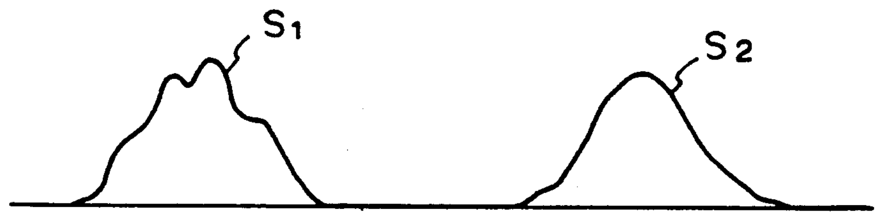
Figure 7:
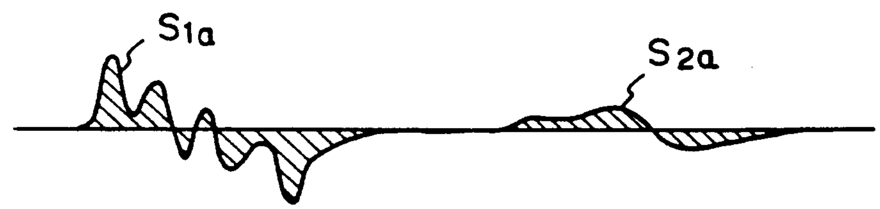

A specific example of means for determining the degrees of complexity and symmetry of a nucleus in a particle will now be described. FIG. 2 is a block diagram illustrating an embodiment of first characteristic quantity extracting means 50 for determining the degree of complexity of a nucleus and second characteristic quantity extracting means 52 for determining the degree of symmetry of a nucleus. A particle signal (hereinafter referred to as a first particle signal) obtained by detecting scattered light along the +Y axis enters a differentiator 62. As shown in FIG. 6, the particle signal of a white blood cell having a nucleus whose lobes have developed has a complex waveform which is very uneven, as shown at $S_1$, while the particle signal of a white blood cell having a nucleus whose lobes have not developed has smooth waveform, as shown at $S_2$. By differentiating these particle signals $S_1$, $S_2$ in the differentiator 62, the components in the high-frequency region of the respective particle signals are emphasized to extract signals $S_1a$, $S_2a$ shown in FIG. 7, respectively. The areas (indicated by the shaded portions) of the differentiated signals $S_1a$, $S_2a$ correspond to the complexities of the particle signals $S_1$, $S_2$, respectively. Accordingly, the differentiated signals $S_1a$, $S_2a$ are full-wave rectified by a rectifier 64 and then integrated by an integrator 66, thereby obtaining an analog signal corresponding to the aforementioned area. This signal is converted into digital data by an A/D converter 68. Thus, the degree of complexity of the waveform of the first particle signal is converted into a numerical value simply and accurately. Thereafter, all circuit elements return to their initial states.

Figure 8:
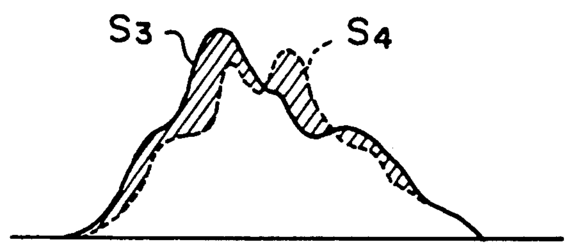
FIG. 8 is a diagram for describing the second characteristic quantity extracting means, this diagram showing two types of particle.

A particle signal (hereinafter referred to as a second particle signal) obtained by detecting scattered light along the −Y axis is used in order to determine the difference between itself and the first particle signal. As shown in FIG. 8, the difference between the first particle signal $S_3$ and second particle signal $S_4$ corresponds to an area indicated by hatched portion. The first and second particle signals both enter a subtracter 70, which calculates the difference between the signals. The resulting difference signal is full-wave rectified by a rectifier 72, whose output is integrated by an integrator 74. The integrated signal is then converted into digital data by an A/D converter 76. The magnitude of the difference between the first and second particle signals is thus converted into a numerical value simply and accurately. All circuit elements then return to their initial states. Thus, a lobe index B indicating the lobe state of every single white blood cell is defined and determined, by arithmetic operations, from data F(1) indicating the complexity of a particle nucleus and data T(1,2) indicating the symmetry of the particle nucleus, these data F(1), T(1,2) being quantified upon extraction from the two types of particle signals. For example, B can be determined as follows:

$$B = K[F(1) + T(1,2)] + C, \text{ or}$$

$$B = \sqrt{F(1)^2 + T(1,2)^2} + C.$$

Alternatively, it is also possible to obtain the complexity of the second particle signal using the first characteristic quantity extracting means and employ the complexity data F(1) obtained from the first particle signal and complexity data F(2) obtained from the second particle signal. For example, B can be determined as follows:

$$B = K\left[\frac{F(1) + F(2)}{2} + T(1,2)\right] + C,$$

$$B = K\sqrt{\left(\frac{F(1) + F(2)}{2}\right)^2 + T(1,2)^2} + C,$$

$$B = K\{\text{Max}[F(1), F(2)] + T(1,2)\} + C, \text{ or}$$

$$B = K\sqrt{\{\text{Max}[F(1), F(2)]\}^2 + T(1,2)^2} + C.$$

$$\text{Here Max}[F(1), F(2)] = \begin{cases} F(1); & F(1) \geqq F(2) \\ F(2); & F(1) < F(2) \end{cases}$$

The nuclear shift index can also be well expressed as follows:

$$B = K[F(1) + F(2)] + C, \text{ or}$$

$$B = K\sqrt{F(1)^2 + F(2)^2},$$

where K and Ç are constants.

Figure 3:
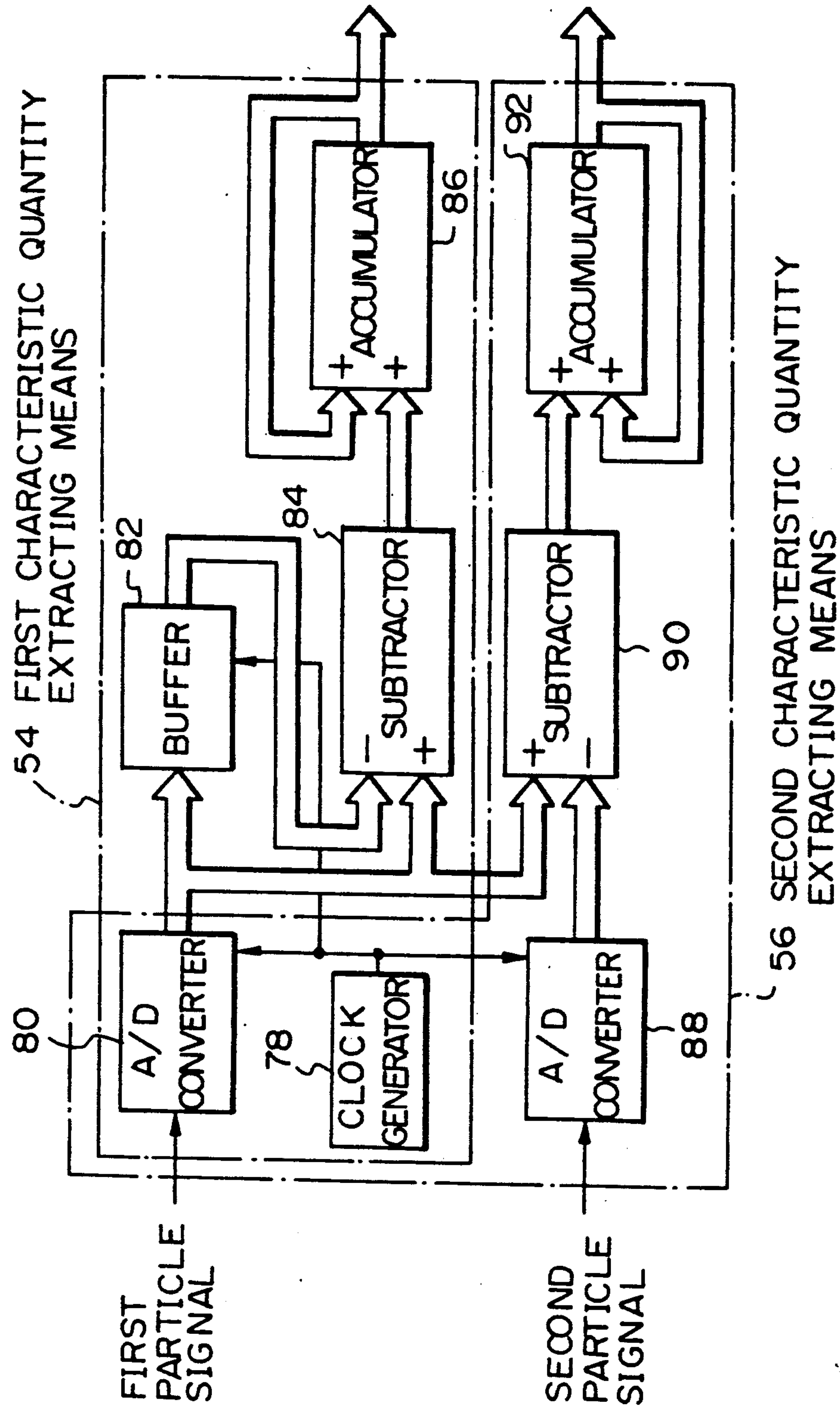

FIG. 3 is a block diagram showing an arrangement in which the signal processing of FIG. 2 is implemented by digital signal processing. The technical concept is the same as that of the block diagram shown in FIG. 2.

A clock generator 78 supplies clock pulses at equal time intervals at a rate quicker than that at which the particle signal changes. The first particle signal enters a high-speed A/D converter 80, the second particle signal enters a high-speed A/D converter 88, and both particle signals are sampled and converted into digital data in response to every clock pulse. The sampling data indicative of the first particle signal enter a buffer 82 serving as temporary storage means, whereby these data are temporarily preserved and outputted at every clock. Sampling data, which prevail at the present time, outputted by the A/D converter 80 and sampling data, which prevailed one clock interval earlier than the present time, enter a subtracter 84, which outputs the absolute value of the difference between the two items of sampling data. By way of example, the subtracter 84 can be one which performs computation by addition based on complementary numbers. For instance, subtraction processing is performed by re-expressing the sampling data from the buffer 82 as a twos complement and adding the sampling data from the A/D converter 80. The sign of the results of this processing is detected in the form of a sign bit. If the sign is negative, the data is re-expressed as a twos complement and converted into an absolute value. The absolute value of the difference between both items of data (present-time sampling data and sampling data one time interval earlier than the present time) is thus determined. The data outputted by the subtracter 84 are applied to an accumulator 86 to be cumulatively added thereby. All circuit elements then return to their initial states.

Figure 13:
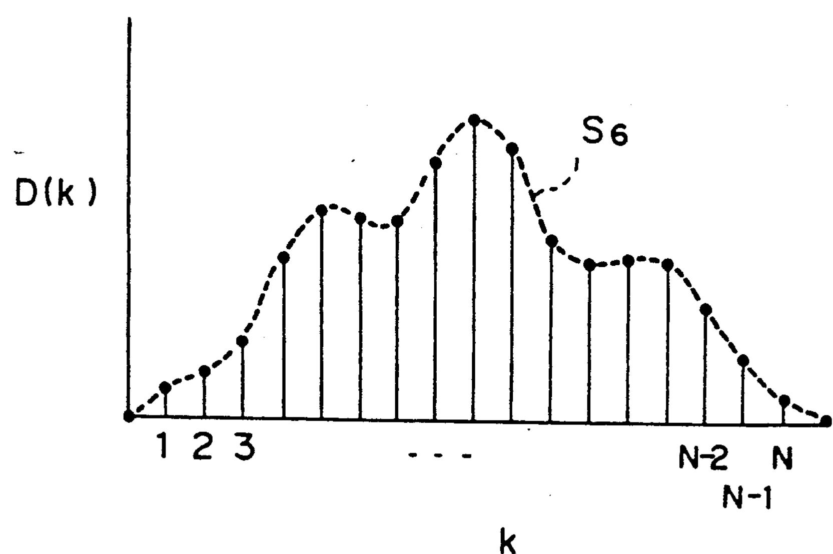
FIG. 13 is a diagram illustrating the sampling of a particle signal.

FIG. 13 is a view for describing the foregoing. A particle signal $S_6$ is sampled and A/D converted every sampling clock, whereby digital data D(1), D(2), . . . , D(N) indicative of the particle signal are successively obtained. These data are processed by the buffer 82 and subtracter 84 to successively obtain absolute values of the difference between $|D(k)-D(k-1)|$, where k=1, 2, . . . , N. A cumulative value $$\sum_{k=1}^{N} |D(k) - D(k-1)|$$

is determined by the accumulator 86.

The first particle signal sampling data and second particle signal sampling data outputted by the A/D converters 80, 88, respectively, enter a subtracter 90. In a manner similar to that described above, the absolute value of the difference between these two items of data is obtained and the absolute values are cumulatively added by an accumulator 92. By thus adopting digital signal processing, measurement precision is improved and the system is made less susceptible to noise.

Figure 9:
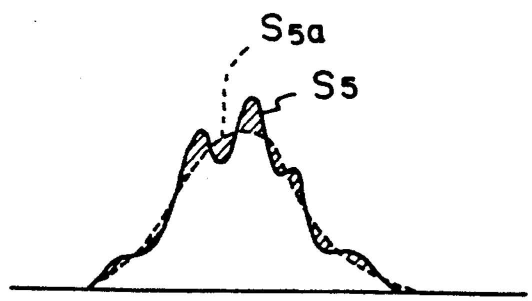
FIG. 9 is a diagram for describing another embodiment of the first characteristic quantity extracting means, this diagram showing a signal obtained by eliminating components in a high-frequency region from the particle signal, as well as the original particle signal.
Figure 10:
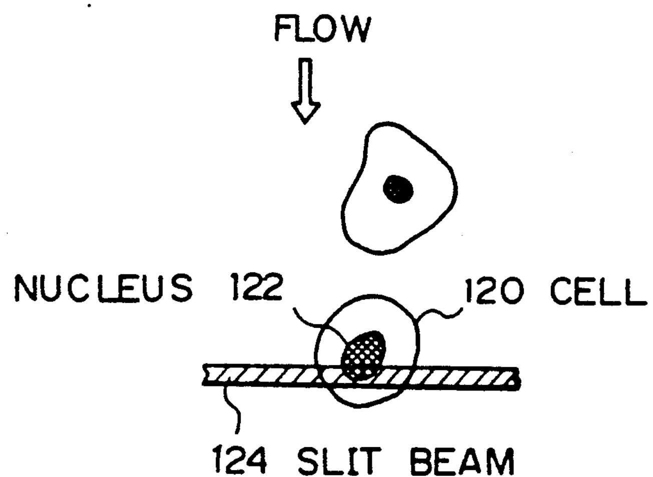
Figure 11:
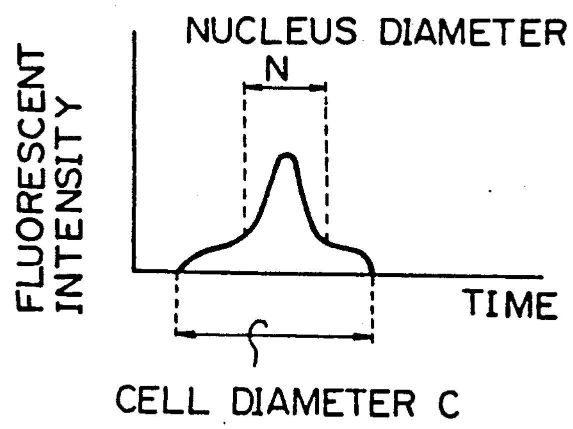
Figure 12:
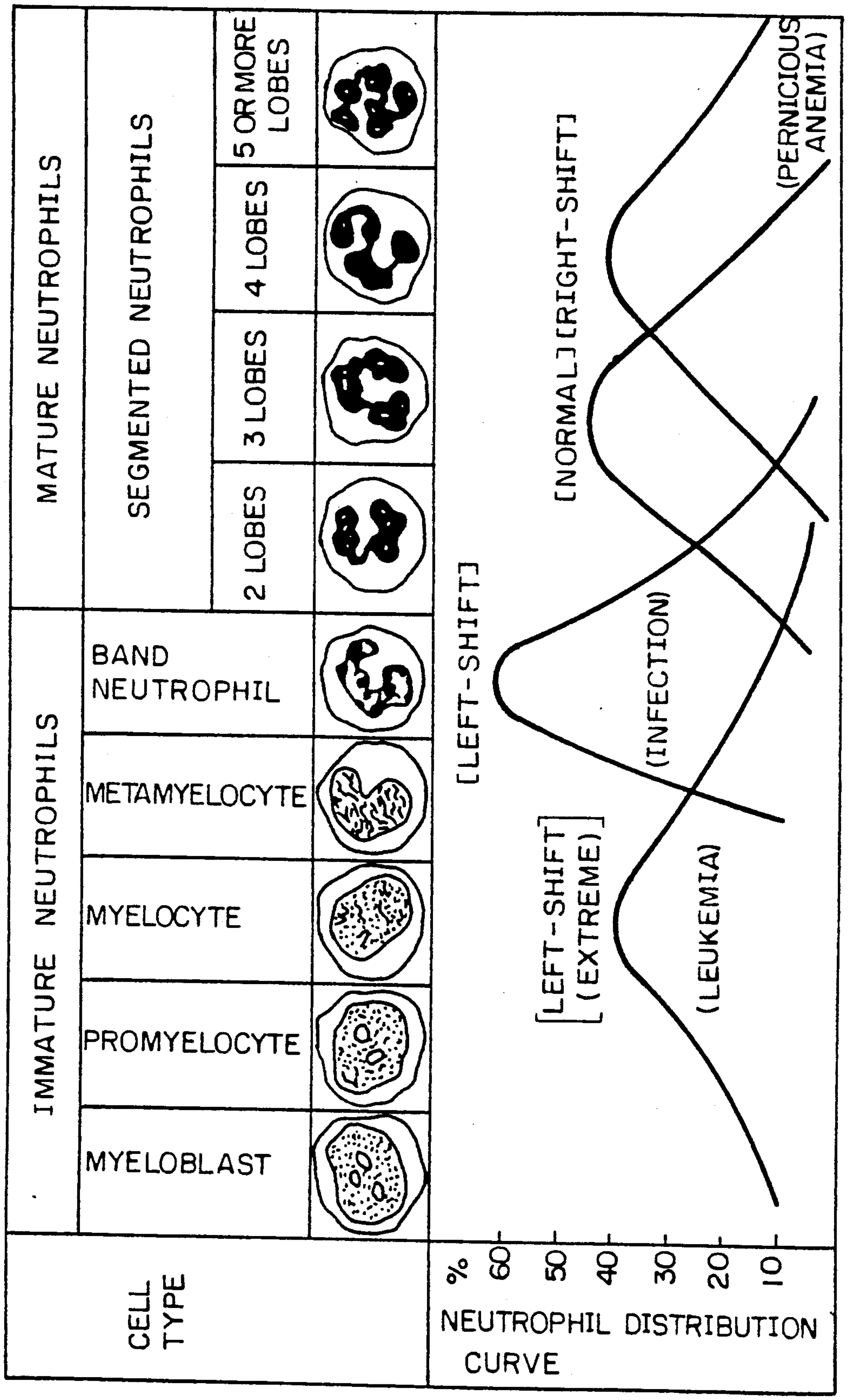
FIG. 12 is a view illustrating the lobes of neutrophil nuclei.

The following approach can also be adapted in order to obtain the complexity of the particle signal waveform as a numerical value: As shown in FIG. 9, signal components in the high-frequency region can be removed from the particle signal $S_5$ by calculating the difference between the particle $S_5$ and the signal $S_5a$, which is obtained by eliminating signal components in the high-frequency region from the particle signal $S_5$. The area (the shaded portion) of the difference can be adapted as representing the complexity of the waveform of particle signal $S_5$. The means for accomplishing this will now be described.

Figure 4:
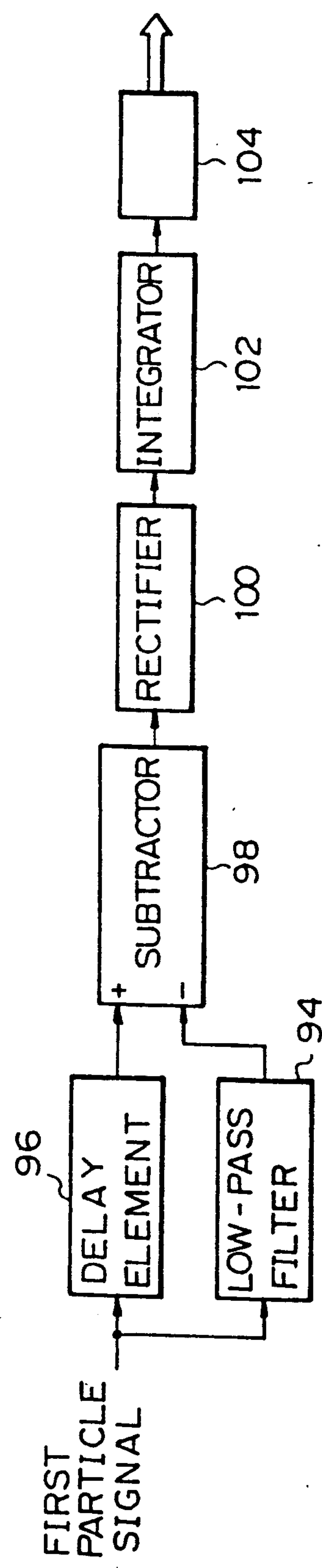
FIGS. 4 and 5 are block diagrams illustrating other embodiments of the first characteristic quantity extracting means.

FIG. 4 is a block diagram showing another embodiment of the first characteristic quantity extracting means. Here the differentiator 62 in FIG. 2 is replaced by a low-pass filter 94, a delay element 96 and a subtracter 98. The first particle signal enters the low-pass filter 94 and the delay element 96. The particle signal applied the low-pass filter has its high-frequency components removed, whereby ripple is removed from the waveform to obtain a waveform which is smooth. The delay element 96 subjects the particle signal to a phase delay equivalent to that produced by the action of the low-pass filter 94. The original signal and the signal outputted by the low-pass filter 94, which are now in phase, enter the subtracter 98, which calculates the difference between them. The resulting signal is full-wave rectified by a rectifier 100, whose output is integrated by an integrator 102. The integrated output is converted into a digital numerical value by an A/D converter 104.

Figure 5:
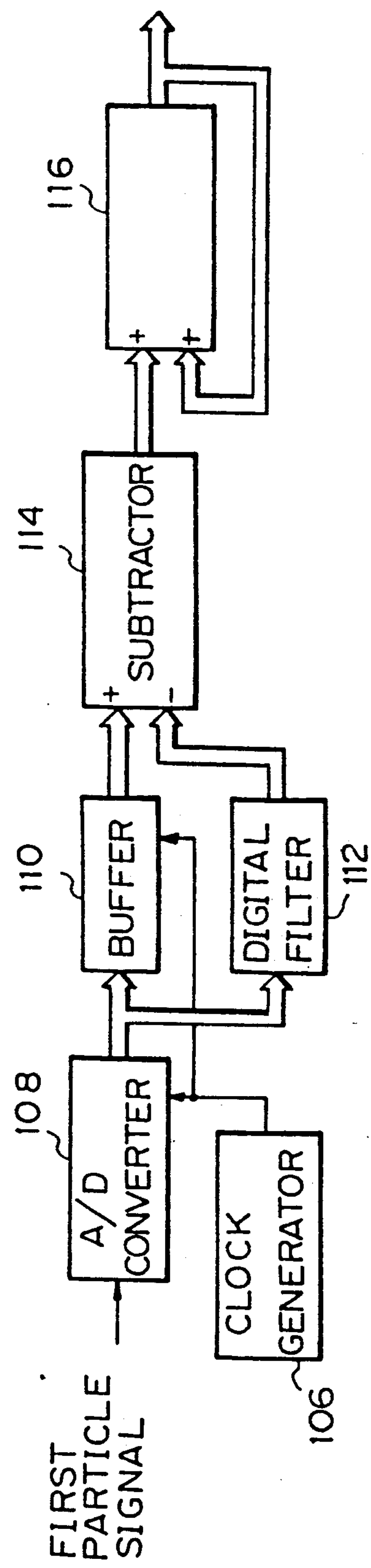

FIG. 5 is a block diagram illustrating another embodiment of the first characteristic quantity extracting means. Here the function of the first characteristic quantity extracting means shown in FIG. 4 is implemented by digital signal processing. The technical concept is the same as that of the block diagram shown in FIG. 4. The particle signal is sampled and digitized by a high-speed A/D converter 108 in response to every clock pulse issued by a clock generator 106. The digitized particle signal is delivered to a buffer 110 serving as temporary memory means, and the signal data are successively outputted after being temporarily stored in sync with the clock pulses. The digitized particle signal is also delivered to a digital filter 112, the action of which is the same as that of a low-pass filter. The digital filter 112 can be constituted by a multiplier, accumulator and the like or can be implemented by software. The temporarily stored digital signal and the filtered digital signal are successively delivered to a subtracter 114, which successively calculates the absolute value of the difference between the two signals. The resulting absolute values are accumulated by an accumulator 116.

Thus, an index is obtained that indicates the lobe degree of individual particles. Since other means can be employed to individually determine, say, the peak values of particle signals, a demarcation line can be drawn on a distribution in which peak value is plotted along the horizontal axis and frequency along the vertical axis, thus enabling neutrophils to be distinguished from other white blood cells. This makes it possible to provide valuable clinical information, such as a lobe index distribution and mean lobe index regarding particles indentified as being neutrophils.

When the optical system of FIG. 1 is used, the apparatus can be arranged to detect fluorescence of different wavelengths using a dye which stains each white blood cell in conformity with the type thereof. Each white blood cell can be classified by respectively determining the peak values or area values of the different types of particle signals, obtaining a two-dimensional distribution in which fluorescents of different wavelengths or fluorescent and the above-mentioned scattered light are taken as the axes, and providing a demarcation line on the distribution.

By making overall use of the nuclear shift indices of individual particles obtained by the particle analyzing apparatus and method of the present invention, the particles can be classified and counted more precisely. This can be effectively exploited in accurately detecting and assessing abnormal particles.

In accordance with the particle analyzing technique of the present invention as described above, a particle is irradiated with a laser beam formed to be narrower than the diameter of the particle nucleus in the direction of particle flow and wider than the diameter of the particle in a direction perpendicular to the particle flow, two side-scattered light beams emitted by the particle in directions symmetrical with respect to the optic axis of the laser beam are detected, and the detected side-scattered light beams are utilized as particle signals. This makes it possible to obtain information that better reflects the structure of the nucleus within the particle. Also, nuclear complexity and symmetry useful in obtaining nuclear shift index are determined by first and second characteristic quantity extracting means, respectively, and the data indicative of nuclear complexity and symmetry are used to accurately determine, for individual particles, an index (shift index) which well expresses the lobe state of the particle nucleus. This can be accomplished through simple calculation and without relation to the orientation of particles undergoing analysis in the particle flow. By making comprehensive use of the index, a particle measurement technique can be realized that is extremely valuable in terms of clinical examination.

The first characteristic quantity extracting means in claim 1 of the claims is simple in construction and accurately determines the complexity of a particle nucleus. In accordance with claim 3, the first characteristic quantity extracting means is such that the means of claim 2 is implemented digitally. It also serves to improve measurement precision and make the apparatus less susceptible to noise.

The second characteristic quantity extracting means in claim 4 of the claims is simple in construction and accucurately determines the symmetry of a particle nucleus. In accordance with claim 5, the second characteristic quantity extracting means is such that the means of claim 4 is implemented digitally. It also serves to improve measurement precision and make the apparatus much less susceptible to noise.

As many apparently widely different embodiments of the present invention can be made without departing from the spirit and scope thereof, it is to be understood that the invention is not limited to the specific embodiments thereof except as defined in the appended claims.

What is claimed is:

1. A particle analyzing apparatus for determining a nuclear shift index of a particle, the apparatus forming a detecting zone by irradiating a zone, in which particles flow substantially in single file, with a laser beam in a direction perpendicular to the direction of particle flow and detecting, at a plurality of locations, an optical change produced in the detecting zone when particles pass through the detecting zone one at a time, thereby obtaining plural types of signals with respect to a single particle, said apparatus comprising:

laser beam means in a laser beam irradiating zone for irradiating a particle with a laser beam to scatter light therefrom conforming to the structure of the particle nucleus, the laser beam formed to be narrower than the diameter of a particle nucleus in the direction of particle flow and wider than the diameter of the particle in a direction perpendicular to the particle flow;

photo-detecting means for detecting two types of particle signals with respect to a single particle by respectively detecting side-scattering light beams produced in directions symmetrical with respect to the optic axis of the laser beam;

first characteristic quantity extracting means for extracting the amount of high-frequency components which are contained in at least one type of particle signal of the two types of particle signals, in order to determine the degree of complexity of the particle nucleus shape; and second characteristic quantity extracting means for extracting the magnitude of a difference between the two types of particle signals in order to determine the degree of symmetry of the particle nucleus shape.

2. The apparatus according to claim 1, wherein said first characteristic quantity extracting means comprises:

a differentiator for differentiating an inputted particle signal;

a rectifier connected to an output side of said differentiator for full-wave rectifying an output signal thereof;

an integrator connected to an output side of said rectifier for integrating an output signal thereof; and an A/D converter connected to an output side of said integrator for converting an analog output thereof into digital data.

3. The apparatus according to claim 1, wherein said first characteristic quantity extracting means comprises:

an A/D converter for sampling and successively converting the inputted particle signal into digital data at equally spaced clock pulses;

memory means connected to an output side of said A/D converter for temporarily storing the digital data;

a subtracter connected to the output side of said A/D converter and an output side of said memory means for successively calculating the absolute value of a difference between data, which prevails at the present time, outputted by said A/D converter and data, which prevailed one clock interval earlier than the present time, outputted by said memory means; and an accumulator connected to an output side of said subtracter for successively cumulatively adding output value data outputted by said subtracter.

4. The apparatus according to claim 1 wherein said second characteristic quantity extracting means comprises:

a subtracter for obtaining the difference between the inputted two types of particle signals;

a rectifier connected to an output side of said subtracter for full-wave rectifying an output signal thereof;

an integrator connected to an output side of said rectifier for integrating a rectified output signal thereof; and an A/D converter connected to an output side of said integrator for converting an integrated analog output thereof into digital data.

5. The apparatus according to claim 1 wherein said second characteristic quantity extracting means comprises:

an A/D converter for sampling and successively converting each of the inputted two types of particle signals into digital data at equally spaced clock pulses;

a subtracter connected to an output side of said A/D converter for successively calculating the absolute value of a difference between both items of digital data; and an accumulator connected to an output side of said subtracter for successively cumulatively adding absolute value data outputted by said subtracter.

6. A particle analyzing method comprising the steps of:

irradiating a particle in an irradiating zone with a laser beam to scatter light therefrom conforming to the structure of the particle nucleus;

forming the laser beam to be narrower than the diameter of a particle nucleus in the direction of particle flow and wider than the diameter of the particle in a direction perpendicular to the particle flow;

detecting, as a plurality of particle signals based on a single particle, two side-scattered light beams generated in directions symmetrical with respect to the optic axis of the laser beam;

extracting data from the particle signals which is indicative of the degrees of complexity and symmetry of a nucleus of the particle; and calculating a nuclear shift index for every single particle using the data indicative of the degree of complexity and the data indicative of the degree of symmetry.

7. A particle analyzing apparatus for determining a nuclear shift index of a particle, the apparatus forming a detecting zone by irradiating a zone, in which particles flow substantially in single file, with a laser beam in a direction perpendicular to the direction of particle flow and detecting, at a plurality of locations, an optical change produced in the detecting zone when particles pass through the detecting zone one at a time, thereby obtaining plural types of signals with respect to a single particle, said apparatus comprising:

a laser beam irradiating zone for performing irradiation with the laser beam formed to be narrower than the diameter of a particle nucleus in the direction of particle flow and wider than the diameter of the particle in a direction perpendicular to the particle flow;

photo-detecting means for detecting two types of particle signals with respect to a single particle by respectively detecting side-scattering light beams produced in directions symmetrical with respect to the optic axis of the laser beam;

first characteristic quantity extracting means for extracting the amount of high-frequency components, which are contained in at least one type of particle signal of the two types of particle signals, in order to determine the degree of complexity of the particle nucleus, said first characteristic quantity extracting means comprising a differentiator for differentiating an inputted particle signal, a rectifier connected to an output side of said differentiator for full-wave rectifying an output signal thereof an integrator connected to an output side of said rectifier for integrating an output signal thereof, and an A/D converter connected to an output side of said integrator for converting an analog output thereof into digital data; and second characteristic quantity extracting means for extracting the magnitude of a difference between the two types of particle signals in order to determine the degree of symmetry of the particle nucleus.

8. The apparatus according to claim 7, wherein said second characteristic quantity extracting means comprises:

a subtracter for obtaining the difference between the inputted two types of particle signals;

a rectifier connected to an output side of said subtracter for full-wave rectifying an output signal thereof;

an integrator connected to an output side of said rectifier for integrating a rectified output signal thereof; and an A/D converter connected to an output side of said integrator for converting an integrated analog output thereof into digital data.

9. The apparatus according to claim 7, wherein said second characteristic quantity extracting means comprises:

an A/D converter for sampling and successively converting each of the inputted two types of particle signals into digital data at equally spaced clock pulses;

a subtracter connected to an output side of said A/D converter for successively calculating the absolute value of a difference between both items of digital data; and an accumulator connected to an output side of said subtracter for successively cumulatively adding absolute value data outputted by said subtracter.

10. A particle analyzing apparatus for determining a nuclear shift index of a particle, the apparatus forming a detecting zone by irradiating a zone, in which particles flow substantially in single file, with a laser beam in a direction perpendicular to the direction of particle flow and detecting, at a plurality of locations, an optical change produced in the detecting zone when particles pass through the detecting zone one at a time, thereby obtaining plural types of signals with respect to a single particle, said apparatus comprising:

a laser beam irradiating zone for performing irradiation with the laser beam formed to be narrower than the diameter of a particle nucleus in the direction of particle flow and wider than the diameter of the particle in a direction perpendicular to the particle flow;

photo-detecting means for detecting two types of particle signals with respect to a single particle by respectively detecting side-scattering light beams produced in directions symmetrical with respect to the optic axis of the laser beam;

first characteristic quantity extracting means for extracting the amount of high-frequency components, which are contained in at least one type of particle signal of the two types of particle signals, in order to determine the degree of complexity of the particle nucleus, wherein said first characteristic quantity extracting means comprises an A/D converter for sampling and successively converting the inputted particle signal into digital data at equally spaced clock pulses, memory means connected to an output side of said A/D converter for temporarily storing the digital data, a subtracter connected to the output side of said A/D converter and an output side of said memory means for successively calculating the absolute value of a difference between data, which prevails at the present time, outputted by said A/D converter and data, which prevailed on clock interval earlier than the present time, outputted by said memory means, and an accumulator connected to an output side of said subtracter for successively cumulatively adding output value data outputted by said subtracter; and second characteristic quantity extracting means for extracting the magnitude of a difference between the two types of particle signals in order to determine the degree of symmetry of the particle nucleus.

11. The apparatus according to claim 10, wherein said second characteristic quantity extracting means comprises:

a subtracter for obtaining the difference between the inputted two types of particle signals;

a rectifier connected to an output side of said subtracter for full-wave rectifying an output signal thereof;

an integrator connected to an output side of said rectifier for integrating a rectified output signal thereof; and an A/D converter connected to an output side of said integrator for converting an integrated analog output thereof into digital data.

12. The apparatus according to claim 10 wherein said second characteristic quantity extracting means comprises:

an A/D converter for sampling and successively converting each of the inputted two types of particle signals into digital data at equally spaced clock pulses;

a subtracter connected to an output side of said A/D converter for successively calculating the absolute value of a difference between both items of digital data; and an accumulator connected to an output side of said subtracter for successively cumulatively adding absolute value data outputted by said subtracter.

* * * * *

UNITED STATES PATENT AND TRADEMARK OFFICE
CERTIFICATE OF CORRECTION

PATENT NO. : 5,050,987
DATED : September 24, 1991
INVENTOR(S) : Kosaka

It is certified that error appears in the above-identified patent and that said Letters Patent is hereby corrected as shown below:

ON THE TITLE PAGE:

Insert --[30] Foreign Application Priority Data
Sept. 30, 1988 [JP] Japan.....63-246538--.

Column 5, line 53, after "signals" insert --is extracted--.
Column 5, line 62, after "obtained" insert --.-- (period).
Column 7, line 32, change "throught" to --through--.

Signed and Sealed this

Thirteenth Day of April, 1993

*Attest:*

STEPHEN G. KUNIN

*Attesting Officer*

*Acting Commissioner of Patents and Trademarks*